(12) United States Patent
Gazendam

(10) Patent No.: US 10,668,186 B2
(45) Date of Patent: Jun. 2, 2020

(54) QUENCHED COATING

(71) Applicant: Original G B.V., Hoogezand (NL)

(72) Inventor: Jurjen Gazendam, Hoogezand (NL)

(73) Assignee: Original G B.V., Hoogezand (NL)

( * ) Notice: Subject to any disclaimer, the term of this patent is extended or adjusted under 35 U.S.C. 154(b) by 0 days.

(21) Appl. No.: 15/524,625

(22) PCT Filed: Nov. 5, 2015

(86) PCT No.: PCT/NL2015/050771
§ 371 (c)(1),
(2) Date: May 5, 2017

(87) PCT Pub. No.: WO2016/076707
PCT Pub. Date: May 19, 2016

(65) Prior Publication Data
US 2018/0055974 A1    Mar. 1, 2018

(30) Foreign Application Priority Data
Nov. 13, 2014  (NL) ...................... 2013786

(51) Int. Cl.
| | | |
|---|---|---|
| A61L 27/54 | (2006.01) | |
| C09D 171/02 | (2006.01) | |
| A61L 29/16 | (2006.01) | |
| A61L 31/16 | (2006.01) | |
| A61L 29/06 | (2006.01) | |
| A61L 31/06 | (2006.01) | |
| A61L 27/34 | (2006.01) | |
| A61L 29/04 | (2006.01) | |
| C08L 71/02 | (2006.01) | |
| A61L 29/08 | (2006.01) | |
| A61L 31/10 | (2006.01) | |
| A61L 31/04 | (2006.01) | |
| A61L 27/22 | (2006.01) | |
| A61L 27/18 | (2006.01) | |
| A61L 27/26 | (2006.01) | |
| C09D 189/00 | (2006.01) | |
| C09K 11/07 | (2006.01) | |
| G01N 21/63 | (2006.01) | |

(52) U.S. Cl.
CPC ............... *A61L 27/54* (2013.01); *A61L 27/18* (2013.01); *A61L 27/22* (2013.01); *A61L 27/26* (2013.01); *A61L 27/34* (2013.01); *A61L 29/044* (2013.01); *A61L 29/049* (2013.01); *A61L 29/06* (2013.01); *A61L 29/085* (2013.01); *A61L 29/16* (2013.01); *A61L 31/041* (2013.01); *A61L 31/043* (2013.01); *A61L 31/06* (2013.01); *A61L 31/10* (2013.01); *A61L 31/16* (2013.01); *C08L 71/02* (2013.01); *C09D 171/02* (2013.01); *C09D 189/00* (2013.01); *C09K 11/07* (2013.01); *G01N 21/63* (2013.01); *A61L 2300/606* (2013.01); *A61L 2400/18* (2013.01); *A61L 2420/02* (2013.01)

(58) Field of Classification Search
CPC .................................................... A61L 27/18
See application file for complete search history.

(56) References Cited

FOREIGN PATENT DOCUMENTS

WO    2014098603 A1    6/2014

OTHER PUBLICATIONS

Weissleder et al. Nature Biotechnology, 1999, 17:375-378.*
Elliott et al. JBC, 1986, 261:11259-11265.*

* cited by examiner

*Primary Examiner* — Bin Shen
(74) *Attorney, Agent, or Firm* — N.V. Nederlandsch Octrooibureau; Catherine A. Shultz; Tamara C. Stegmann

(57) ABSTRACT

Described is an object surface coating comprising one or more polymers and a peptide covalently linked to at least one of said one or more polymers, said peptide comprising a) a first cleavage site, wherein said first cleavage site is cleaved by a first compound specifically provided by a microbe belonging to a first group consisting of a limited number of microbial strains, species or genera, and not cleaved by any compound provided by any microbe not belonging to said first group, b) a first fluorescent agent having an emission wavelength of 650-900 nm, c) a first non-fluorescent agent having an absorption wavelength of 650-900 nm, for quenching said emission of said first fluorescent agent, wherein cleavage of said first cleavage site results in the release of said first non-fluorescent agent from the coating, the release of said first non-fluorescent agent being indicative for the presence of a microbe belonging to said first group.

15 Claims, No Drawings
Specification includes a Sequence Listing.

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence

<400> SEQUENCE: 1

Glu Phe Arg Ile Lys
1               5

<210> SEQ ID NO 2
<211> LENGTH: 5
<212> TYPE: PRT
<213> ORGANISM: Artificial Sequence
<220> FEATURE:
<223> OTHER INFORMATION: Amino acid sequence

<400> SEQUENCE: 2

Asp Phe Arg Ile Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Amino Acid sequence

<400> SEQUENCE: 3

Gly Ile Gly Glu Phe Arg Ile Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Amino acid sequence

<400> SEQUENCE: 4

Gly Ile Gly Asp Phe Arg Ile Lys
1               5

<210> SEQ ID NO 5
<211> LENGTH: 10
<212> TYPE: PRT
<213> ORGANISM: Artificial Sequence
<220> FEATURE:
<223> OTHER INFORMATION: amino acid sequence

<400> SEQUENCE: 5

Gly Leu Leu Glu Phe Arg Ile Val Ala Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Amino acid sequence

<400> SEQUENCE: 6

Gly Leu Leu Glu Phe Arg Ile Val Ala Cys
1               5                   10

```
<210> SEQ ID NO 7
<211> LENGTH: 9
<212> TYPE: PRT
<213> ORGANISM: Artificial Sequence
<220> FEATURE:
<223> OTHER INFORMATION: amino acid sequence

<400> SEQUENCE: 7

Leu Leu Glu Phe Arg Ile Val Ala Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Amino acid sequence

<400> SEQUENCE: 8

Leu Leu Glu Phe Arg Ile Val Ala Lys
1               5

<210> SEQ ID NO 9
<211> LENGTH: 9
<212> TYPE: PRT
<213> ORGANISM: Artificial Sequence
<220> FEATURE:
<223> OTHER INFORMATION: amino acid sequence

<400> SEQUENCE: 9

Leu Leu Glu Phe Arg Ile Val Ala Lys
1               5
```

QUENCHED COATING

REFERENCE TO AN ELECTRONIC SEQUENCE LISTING

The contents of the electronic sequence listing (sequence-listing.txt; Size: 934 bytes; and Date of Creation: Oct. 30, 2017) is herein incorporated by reference in its entirety.

The present invention relates to an object surface coating, a method of preparing an object surface coating as well as the use of a object surface coating for the detection of microorganisms.

The growth of pathogenic microorganisms on surfaces, for example medical devices and food preparation surfaces leads to the development of infections. Currently there are no means to cheaply and rapidly detect the presence of pathogenic microorganisms on medical devices and food preparation surfaces. The current standard for detecting the presence of microorganisms on surface is via a microbiological culture taken from a sample suspected to be contaminated. Implanted medical devices need to be removed prior to collecting a sample for culture. Disadvantages of such a tests are that they are time consuming, costly and labour intensive, and require the removal of the implant.

Attempts to overcome such problems with respect to medical devices are known in the prior art. For example U.S. Pat. No. 6,306,422 describes an implant coated with a hydrogel matrix, comprising embedded releasable active agents, such as therapeutic and/or diagnostic agents, due to environmental changes. By a pH change in the host at the location of the implant, the embedded active agents are released.

A drawback of such implants is that the implant is not responsive to a specific pathogenic microbe and thus false positives are possible due to purely environmental and not microbial causes.

Object surface coatings for the detection of microorganisms are known in the prior art. WO2014098603 describes the release of therapeutic and/or diagnostic agents from a object surface coating in the presence of specific pathogenic microbes. A drawback of such a coating is that a fluorescent agent is released into the matrix or surrounding area. Detection of the released fluorescent agent is thus dependent on diffusion away from the surface coating. In cases of slow diffusion, a false negative may result.

It is an aim of the present invention to solve the problems of object surface coatings in the art.

The present invention provides a object surface coating object surface coating comprising one or more polymers and a peptide covalently linked to at least one of said one or more polymers, said peptide comprising:

a) a first cleavage site, wherein said first cleavage site is cleaved by a first compound specifically provided by a microbe belonging to a first group consisting of a limited number of microbial strains, species or genera, and not cleaved by any compound provided by any microbe not belonging to said first group, b) a first fluorescent agent having an emission wavelength of 650-900 nm, c) a first non-fluorescent agent having an absorption wavelength of 650-900 nm, for quenching said emission of said first fluorescent agent, wherein cleavage of said first cleavage site results in the release of said first quencher agent from the coating, the release of said first agent being indicative for the presence of a microbe belonging to said first group.

The present invention provides an object surface coating comprising:

a) one or more polymers, b) a first fluorescent agent having an emission wavelength of 650-900 nm, c) a first non-fluorescent agent having an absorption wavelength of 650-900 nm, for quenching said emission of said first fluorescent agent, d) a peptide covalently linked to at least one of said one or more polymers, said peptide comprising the first non-fluorescent agent having an absorption wavelength of 650-900 nm, for quenching said emission of said first fluorescent agent and a first cleavage site, wherein said first cleavage site is cleaved by a first compound specifically provided by a microbe belonging to a first group consisting of a limited number of microbial strains, species or genera, and not cleaved by any compound provided by any microbe not belonging to said first group, wherein cleavage of said first cleavage site results in the release of said first non-fluorescent agent from the coating, the release of said first non-fluorescent agent being indicative for the presence of a microbe belonging to said first group.

The invention provides an object surface coating in which the cleavage of the first cleavage site simultaneously results in the cleavage of the first non-quenching agent from the object surface coating so that the emission of the first fluorescent agent can be detected.

In a preferred embodiment, cleavage of the first cleavage site does not result in release of the first fluorescent agent from the object surface coating. In other words, after cleavage of the first cleavage site, the first fluorescent agent remains covalently bound to the object surface coating.

The effect of only releasing the first non-fluorescent agent from the object surface coating is that the object surface coating alters its state from being "dark", that is emits no light of wavelength 650-900 nm, to a "light" state, that emits light of wavelength 650-900 nm, which emitted light can be recorded by suitable detector. An advantage of such an alteration from a "dark (off)" state to a "light (on)" state is that the chance of false positives is reduced.

For example, in the coatings of the prior art which do not comprise a non-fluorescent moiety according to the present invention, an object surface coating emits light in the absence of microorganisms but in the presence of microorganisms the fluorescent agent is released from the coating and the coating changes to a dark state in which no light is emitted. However, in this case the object surface coating could still emit light if the first fluorescent agent does not diffuse away from the coating, thus a false result would be observed. In the coating according to the present invention the chance of such false positives is reduced because as soon as cleavage occurs, the distance between the first fluorescence agent and first non-fluorescent agent increases such that the emission is no longer quenched.

Without wishing to be bound by theory, releasing the first non-fluorescent agent from an object surface coating means that quenching of the light emitted from the first fluorescent agent is not dependent on the diffusion of the first fluorescent agent away from the object surface coating as in coatings of the prior art.

This cleavage is effected by a compound, provided by a microbe, belonging to a group consisting of a limited number of microbial strains, species or genera. Members of this group, as a matter of ease indicated as the first group, of microbial strains, species or genera are capable of specifically providing a compound, that cleaves the said first cleavage site. The term 'specifically' means that microbial strains, species or genera not belonging to the said first group are not capable of providing a compound that can recognize and cleave the said cleavage site, in contrast to members of said first group. The compound can be provided e.g. by release of the said compound from a microbe, or can e.g. be presented on the outer surface thereof. In the latter case, cleavage will be effected upon contact of the microbe with the coating, whereas when the compound is released from the microbe, the microbe can be at a distance of the coated object, as long as the released compound is capable to arrive at the coating after release from the microbe.

It is also possible for the microbe belonging to a certain group, upon infection of a host, to induce the release or production of a particular compound by the host. In the latter case, this compound is not produced or released by the host upon infection of another microbe, not belonging to the said group. Cleavage can be effected by the compound, or can e.g. be induced by binding of the said compound forming a complex, which complex is recognized by a cleaving factor, present in the environment of the coating, i.e. provided by the microbe or a host infected by the microbe and comprising the object. For microbes to belong to a certain group, such as the first group of strains, species, or genera, the presence of these microbes must induce cleavage of the cleavage site, whereas cleavage is not induced by microbes from another group. This cleavage can occur by the same compound, but also by a plurality of different compounds, as long as these compounds induce cleavage of the said same cleavage site. For example, the first group comprises three different bacterial species, the first and second species providing the same compound cleaving the cleavage site of the coating, the third species providing a compound, differing from the compound from the first and second species, but also specifically cleaving the same cleavage site in the coating. The term 'limited' means that such a group will not comprise all microbes, or all bacteria, but to less i.e. a limited number, so that the release of the first agent is indeed indicative for one or more microbes, but not to all or any microbes or bacteria etc.

In an embodiment, the first fluorescent agent has an emission wavelength of 300-450 nm, preferably 450-650 nm, even more preferably 650-900 nm.

The first fluorescent agent having an emission wavelength of 650-900 nm can be any compound which emits light at the required wavelength of 650-900 nm and which has spectral overlap with the first non-fluorescent agent so that when the first fluorescent agent and first non-fluorescent agents are both present on the uncleaved peptide in the object surface coating, no light is emitted.

In an embodiment, the first fluorescent agent having an emission wavelength of 450-650 nm can be any compound which emits light at the required wavelength of 450-650 nm and which has spectral overlap with the first non-fluorescent agent so that when the first fluorescent agent and first non-fluorescent agents are both present on the uncleaved peptide in the object surface coating, no light is emitted.

In another embodiment, the first fluorescent agent having an emission wavelength of 300-350 nm can be any compound which emits light at the required wavelength of 300-350 nm and which has spectral overlap with the first non-fluorescent agent so that when the first fluorescent agent and first non-fluorescent agents are both present on the uncleaved peptide in the object surface coating, no light is emitted.

The first non-fluorescent agent having an absorption wavelength of 650-900 nm, is a compound that has little or no intrinsic fluorescence and which can efficiently quench the fluorescence from a proximate NIR fluorophore with little background are needed. In an embodiment the first non-fluorescent dye is a cyanine molecule. Cyanine molecules, also referred to as cyanine dyes, include compounds having two substituted or unsubstituted nitrogen-containing heterocyclic rings joined by a polymethine chain (Formula I):

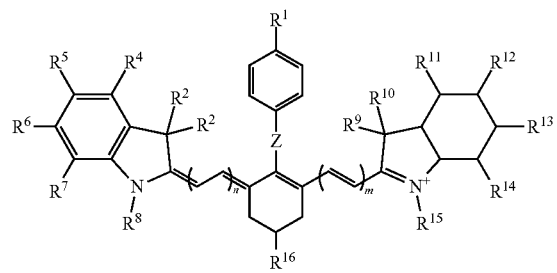

Formula I

In an embodiment, the first fluorescent agent is a cyanine dye having the general formula as shown in formula I, wherein $R^1$ is selected from the group consisting of H, hydrocarbyl, halo, carboxyl, amino and $SO_3^-$ $Cat^+$ wherein $Cat^+$ is a cation, preferably an alkali earth metal, preferably sodium, potassium or lithium; Z is selected from the group consisting of H O, S, NH and N-hydrocarbyl; $R^2$, $R^3$ $R^9$, $R^{10}$ are each independently selected from the group consisting of H and hydrocarbyl, $R^4$, $R^5$ $R^{11}$, $R^{12}$ are each independently selected from the group consisting of H, hydrocarbyl and sulfanato or together with the atoms to which they are bonded form an aromatic ring; $R^6$, $R^7$ $R^{13}$, $R^{14}$ are each independently selected from the group consisting of H and hydrocarbyl, or together with the atoms to which they are bonded form an aromatic ring; $R^8$ and $R^{15}$ are each independently selected from the group consisting of hydrocarbyl, $(CH_2)_q FG$ or $(CH_2)_p LN$ wherein at least one of $R^8$ and $R^{15}$ is $(CH_2)_q FG$, wherein q is an integer from 1 to 20 and FG is a functional group that does not directly react with carboxyl, hydroxyl, amino or thiol groups, wherein p is an integer from 1 to 20 and LN is a linker group that reacts with carboxyl, hydroxyl, amino or thiol groups; $R^{15}$ is H or hydrocarbyl.

The first non-fluorescent agent may also be for example BHQ3, (Biosearch) QC-1 (Li-COR.com), or particles comprising such compounds, for example gold nanoparticles and ferro-nanoparticles.

In an embodiment, the one or more polymers are selected from the group consisting of polyethylene glycol, polyethylene glycol diacrylate, polylactide, Polyvinyl alcohol, poly DL-lactide-co-glycolide/polyethylene glycol copolymer and combinations thereof.

It has been found that advantageous polymers for object surface coatings are polyethylene glycol based polymers due to the biocompatiable nature of polyethylene glycol based polymers.

In an embodiment, the peptide is covalently linked via the N- or C-terminus or a side chain to at least one of said one or more polymers by C4-C30 hydrocarbyl linker, preferably via the C-terminus or a side chain, most preferably via the C-terminus.

The term hydrocarbyl as used in the present description means a linker containing hydrogen and carbon atoms; it is linear, branched or cyclic, saturated or unsaturated, such as an alkyl, alkenyl and alkynyl; alicyclic substituent such as cycloalkyl, cycloalkenyl; aromatic. It may be substituted with one or more non-hydrocarbyl substituent groups, for example a heteroatom. A preferred linker is selected from the group consisting of 4, 5, 6 and 7 carbon atoms.

The inventors have found that by covalently linking the peptide via the C terminus to one or more polymers of the object surface coating, the cleavage site is presented in an orientation that facilitates cleavage by a microorganism.

In an embodiment, the object surface coating according to claim any of the preceding claims, wherein the C4-C30 linker comprises a cyclic hydrocarbyl group or a cyclic heterocyclic group, preferably said heterocyclic group is a triazole group.

In an embodiment of the present invention the linker can be installed via reaction of a reactive group at the N- or C-terminus or side chain of the peptide with a complementary reactive group on the polymer. A particularly preferred reactive group is the azide group and a preferred complementary reactive group is the alkyne group. The reaction of the azide and alkyne proceeds in the presence of the first fluorescent and first non-fluorescent agents without unwanted side reactions occurring.

Further examples include various Pd(0)-catalyzed coupling reactions, Staudinger ligation, cycloaddition reactions (Diels-Alder, 1,3-dipolar cycloaddition), reductive alkylation, oxime and hydrazine formation, thiol addition reactions, and oxidative coupling.

In an embodiment, the first cleavage site is cleaved by a compound provided by gram positive bacteria or gram negative bacteria, preferably gram positive bacteria, more preferably from the genera *Staphylococcus, Streptococcus, Enterococcus*, and *Bacillus, Corynebacterium, Nocardia, Clostridium, Actinobacteria*, and *Listeria*.

An advantage of the object surface coating according to the invention is that the coating can be designed in such a way that the coating is only responsive to a certain group of microorganisms. For example, in a preferred embodiment, the first cleavage site is cleaved by a compound provided by gram positive bacteria, such as *Staphylococcus, Streptococcus, Enterococcus*, and *Bacillus, Corynebacterium, Nocardia, Clostridium, Actinobacteria*, and *Listeria*. In a particularly preferred embodiment, the gram positive bacteria are selected from the genera *Staphylococcus, Streptococcus*, more preferably *Staphylococcus*.

In an embodiment, the first cleavage site is cleaved by a compound provided by gram negative bacteria such as *Escherichia coli, Shigella flexneri*, and *Campylobacter jejuni*.

In an embodiment, the first compound is an protease selected from the group consisting of Endoproteinase Glu-C from *Staphylococcus aureus* V8, IgA1 protease, aureolysin.

An example of a compound that is specific for gram positive bacteria is V8 protease form *Staphylococcus aureus*, also known as endoproteinase Glu-C, Glu-C protease, *staphylococcal serine proteinase, Staphylococcus* V8 serine endopeptidase. This protease cleaves specifically at the carboxyl side of aspartate and glutamate residues.

In an embodiment, the first cleavage site comprises a specific amino acid motif preferably being selected from the group consisting of EFRIV, EFRIK (SEQ ID NO: 1), DFRIK (SEQ ID NO: 2), GIGEFRIK (SEQ ID NO: 3), GIGDFRIK (SEQ ID NO: 4).

In a preferred embodiment, the cleavage site comprises an amino acid selected from the group of serine, threonine, arginine, lysine, aspartic acid and glutamic acid, preferably aspartic acid and glutamic acid, said cleavage being comprised in a compound from at least one bacteria selected from the group consisting of *Staphylococcus, Streptococcus, Enterococcus*, and *Bacillus, Corynebacterium, Nocardia, Clostridium, Actinobacteria*, and *Listeria*.

In a preferred embodiment, the cleavage site comprises an amino acid selected from the group of alanine, leucine, valine, isoleucine and proline, cleavage being comprises in a compound from at least one bacteria selected from the group consisting of *Escherichia coli, Shigella flexneri*, and *Campylobacter jejuni*.

The cleavage site is hereby understood to have its well known meaning, that is a portion of molecular structure of the object surface coating, that is cleaved by a specific compound whereby the cleavage site comprises one or more amide bonds.

The cleavage site may have the structure XYZ, wherein X is at least one amino acid, Y is a portion of molecular structure composed of at least two amino acids representing the first cleavage site, and Z is at least one amino acid. The amino acids used may be any amino acid, preferably chosen from the group of naturally occurring amino acids or from the group of synthetic amino acids, in particular derivatives of natural amino acids. The amino acids are preferably those that enable binding of the compound which effects cleavage of the first cleavage site.

In an embodiment, the first cleavage site comprises amino acids which are substrates and or binding sites for proteases secreted by microorganisms such as gram positive bacteria such as *Staphylococcus, Streptococcus, Enterococcus*, and *Bacillus, Corynebacterium, Nocardia, Clostridium, Actinobacteria*, and *Listeria*. In a particularly preferred embodiment, the gram positive bacteria are selected from the genera *Staphylococcus, Streptococcus*, more preferably *Staphylococcus*.

In an embodiment, the first cleavage site is comprises amino acids which are substrates and or binding sites for proteases secreted by microorganisms such as gram negative bacteria such as *Escherichia coli, Shigella flexneri*, and *Campylobacter jejuni*.

The peptide in which the cleavage site is located can comprise for example between 4 and 14, for example amino acids, for example between 5 and 12 amino acids, for example between 6 and 11 amino acids, for example between 7 and 10 amino acids and for example between 8 and 9 amino acids. Preferably, the peptide comprises 6 amino acids, 7 amino acids, 8 amino acids, 9 amino acid or 10 amino acids.

A cleavage site preferably comprises of a number of amino acids, for example at least two, preferably at least three amino acids, more preferably at least four amino acids, even more preferably at least five amino acids, as described in the standard handbook Biochemistry, Ed. L Stryer, $7^{th}$ Edition, 2012, WH Freeman, Part 1, Chapter 2 Protein Composition and Structure. The portion of molecular structure in a cleavage site may also be referred to as an 'amino acid motif.' In the present invention, the cleavage site is designed such that it is recognized by a compound provided by a microbe belonging to a group consisting of a limited number of microbial strains, species or genera.

In a preferred embodiment, the first fluorescent agent is of formula II:

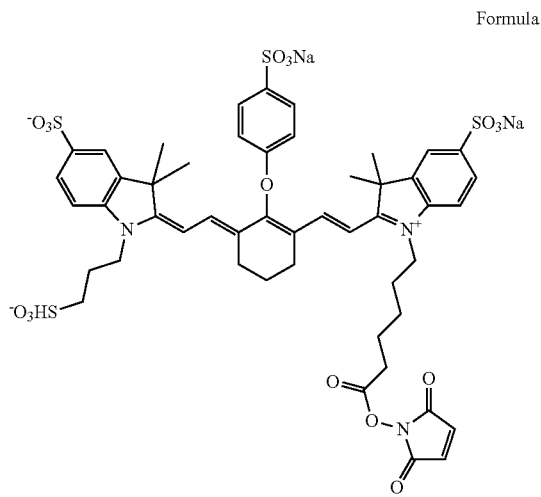

Formula II wherein Z is O, wherein $R^1$ $SO_3^-Na^+$; $R^2$, $R^3$ $R^9$, $R^{10}$ are hydrocarbyl, $R^4$ and $R^{11}$ are H, $R^5$ and $R^{12}$ sulfanato $R^6$, $R^7$ $R^{13}$, $R^{14}$ are H, $R^8$ $(CH_3)_qSO3^-$ and $R^{15}$ $(CH_2)_5$-H-hydroxysuccinimide ester, the first fluorescent agent being tetrasodium 6-(2-{(E)-2-[(3E)-3-{(2E)-2-[3,3-dimethyl-5-sulfonato-1-(4-sulfonatobutyl)-1,3-dihydro-2H-indol-2-ylidene]ethylidene}-2-(4-sulfonatophenoxy)-1-cyclohexen-1-yl]vinyl}-3,3-dimethyl-5-sulfonato-3H-indolium-1-yl)hexanoate and derivatives thereof.

In an embodiment, the derivative of tetrasodium 6-(2-{(E)-2-[(3E)-3-{(2E)-2-[3,3-dimethyl-5-sulfonato-1-(4-sulfonatobutyl)-1,3-dihydro-2H-indol-2-ylidene]ethylidene}-2-(4-sulfonatophenoxy)-1-cyclohexen-1-yl]vinyl}-3,3-dimethyl-5-sulfonato-3H-indolium-1-yl)hexanoate is an amide, carboxylic acid or maleimide.

In an embodiment, the first fluorescent agent, for example a cyanine dye, and/or the first non-fluorescent agent is linked to the peptide via an amide bond, ester or a Michael addition product linkage.

In an embodiment, the first fluorescent agent is a compound according to formula III:

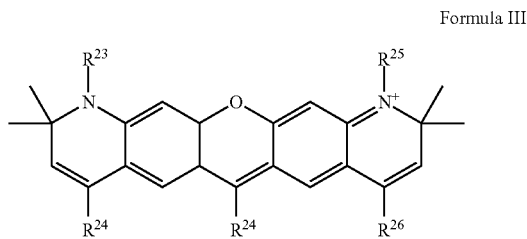

Formula III wherein $R^{23}$ and $R^{25}$ are each independently H or hydrocarbyl, $R^{24}$ and $R^{26}$ are each independently selected from the group consisting of H, hydrocarbyl, and $(CH2)_qFG$, wherein q is an integer from 1 to 20 and FG is a functional group that does not directly react with carboxyl, hydroxyl, amino or thiol groups; $R^{27}$ is each independently selected from the group consisting of H, hydrocarbyl and aryl wherein aryl is optionally substituted by chloro, halo or acyl groups.

Examples of suitable first fluorescent agents that can be used with in present invention include, but are not limited to, Alexa Fluor® 350, Alexa Fluor® 430, Alexa Fluor@ 488, Alexa Fluor® 555, Alexa Fluor® 594, Alexa Fluor® 647, Alexa Fluor@ 660, Alexa Fluor® 680, Alexa Fluor® 700, Alexa Fluor® 750 ATTO 680, ATTO 700, DY-647, DY-650, DY-673, DY-675, DY-676, DY-680, DY-681, DY-682, DY-690, DY-700, DY-701, DY-730, DY-731, DY-732, DY-734, DY-750, DY-751, DY-752, DY-776, DY-781, DY-782, DY-831, La Jolla Blue, Cy5, Cy5.5, Cy7, IRDye® 800CW, IRDye® 38, IRDye® 800RS, IRDye® 700DX, IRDye® 680, among others. "Alexa Fluor" dyes are available from Molecular Probes Inc., Eugene, Oreg., U.S.A. (www.probes.com). "ATTO" dyes are available from ATTO-tec GmbH, Siegen, Germany (www.atto-tec.com). "DY" dyes are available from Dyomics GmbH, Jena, Germany (www.dyomics.com). La Jolla Blue is available from Hyperion Inc. "Cy" dyes are available from Amersham Biosciences, Piscataway, N.J., U.S.A., (www.amersham.com)." IRDye® infrared dyes" are available from LI-COR® Bioscience, Inc., Lincoln, Nebr., U.S.A (www.licor.com).

In an embodiment, the first non-fluorescent agent is a cyanine dye having an absorption wavelength of 650-900 nm. An advantage of cyanine dyes in the near-infra red wavelengths is that near-infrared detection reduces background, scattering and interference caused by other compounds in the sample being measured, improving the reliability of the inventive method in both ex-vivo and in vivo systems. Moreover such wavelengths are able to penetrate tissue making such dyes particularly suitable for in vivo applications.

In a preferred embodiment, the non-fluorescent agent is -Diethylamino-5-phenylphenazium-7-diazobenzene-4"-(N-ethyl-2-O-(4,4'-dimethoxytrityl))-N-ethyl-2-O (BHQ3) (Biosearch), QC-1, IRDye® 800RS (Li-COR.com), gold nanoparticles and ferro-nanoparticles.

In an embodiment, the first non-fluorescent agent is a compound of formula IV:

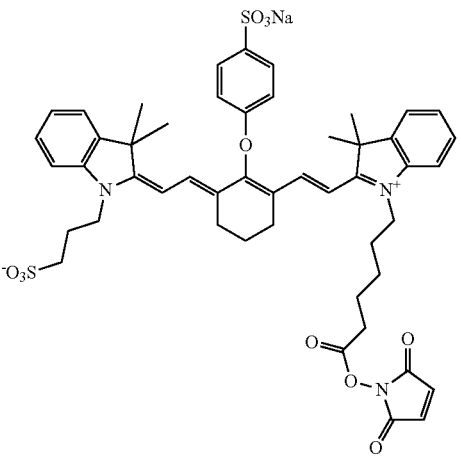

Formula IV wherein Z is O, wherein $R^1$ $SO3^-Na^+$; $R^2$, $R^3$ $R^9$, $R^{10}$ are hydrocarbyl, $R^4$ and $R^{11}$ are $R^5$ and $R^{12}$ are H, $R^6$, $R^7$ $R^{13}$, $R^{14}$ are H, $R^8$ $(CH3)_qSO3^-$ and $R^{15}$ $(CH_2)_5$-H-hydroxysuccinimide ester.

In a preferred embodiment, when the first fluorescent agent is the same as the first non-fluorescent agent, said first fluorescent agent is the compound according to formula IV, IRDye® 800RS. In this embodiment the IRDye® 800RS has the property of self-quenching emitted light in the coating.

When a proportion of the IRDye® 800RS is removed from the coating, there is an increase in the distance between the IRDye® 800RS molecules so that a lower degree of self-quenching occurs and thus light is emitted from the coating.

Alternatively, the first non-fluorescent agent is a compound of formula V:

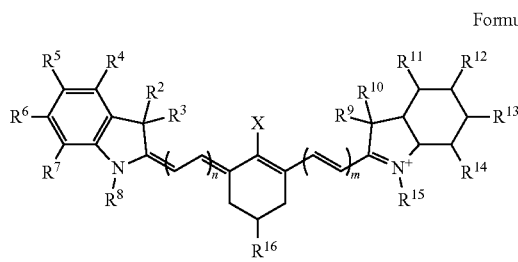

Formula V wherein X is selected from the group consisting of H, chlorine, fluorine, bromine, O-aryl wherein aryl is para-substituted by a group selected from the group consisting of sulfanto, halogen, hydroxyl and amine; $R^2$, $R^3$ $R^9$, $R^{10}$ are each independently H or hydrocarbyl, $R^4$, $R^5$, $R^{11}$, $R^{12}$ are each independently selected from the group consisting of H, hydrocarbyl, sulfanato and N-hydrocarbyl or together with the atoms to which they are bonded form an aromatic ring; $R^6$, $R^7$ $R^{13}$, $R^{14}$ are each independently selected from the group consisting H, sulfanato hydrocarbyl, or together with the atoms to which they are bonded form an aromatic ring; $R^8$ and $R^{15}$ are each independently hydrocarbyl, $(CH_2)_q FG$ or $(CH_2)_p LN$ wherein at least one of $R^8$ and $R^{15}$ is $(CH_2)_q FG$, wherein q is an integer from 1 to 20 and FG is a functional group that does not directly react with carboxyl, hydroxyl, amino or thiol groups, wherein p is an integer from 1 to 20 and LN is a linker group that reacts with carboxyl, hydroxyl, amino or thiol groups; $R^{15}$ is H or hydrocarbyl.

Preferably, the compound of formula V is a compound wherein X is chlorine; $R^2$, $R^3$ $R^9$, $R^{10}$ hydrocarbyl, $R^4$, $R^6$ $R^7$, $R^{11}$ $R^{12}$, $R^{14}$ are H, $R^5$ is N-hydrocarbyl; $R^{13}$ is sulfanato, R8 (CH3)qSO3- and R15 (CH2)5-H-hydroxysuccinimide ester, said first non-fluorescent agent being sodium 4-((E)-6-((E)-2-[3,3-dimethyl-1-(4-sulfonatobutyl)-indolin-2-ylidene]ethylidene}-2-((E)-2-(1-6-(2,5-dioxopyrrolidin-1-yloxy)-6-oxyhexyl)-3,3-dimethyl-3H-indolium-2yl)vinyl) cyclohex-1-enyloxy)benzenesulphonate.

In yet another embodiment, the first non-fluorescent agent is a compound according to formula VI:

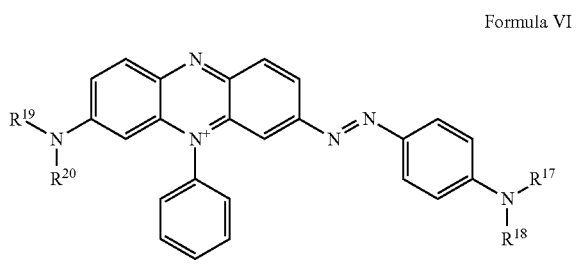

Formula VI wherein $R^{17}$, $R^{18}$, $R^{19}$ and $R^{20}$ are each independently hydrocarbyl or substituted hydrocarbyl wherein the hydrocarbyl is substituted by hydroxyl, halo, phosphor or sulfanato groups.

In a further embodiment, the first non-fluorescent agent is a compound according to formula VII:

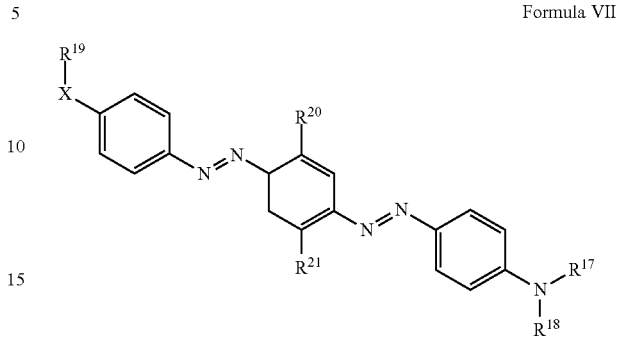

Formula VII wherein $R^{17}$, $R^{18}$ and $R^{19}$ are each independently hydrocarbyl or substituted hydrocarbyl wherein the hydrocarbyl is substituted by hydroxyl, halo, phospho or sulfanato groups; $R^{20}$ and $R^{21}$ are H, hydrocarbyl, alkoxy or halo groups.

In an embodiment, the first non-fluorescent agent has an absorption wavelength of 300-450 nm, preferably 450-650 nm, even more preferably 650-900 nm. The first non-fluorescent agent is selected such that a good spectral overlap with the first fluorescent agent is obtained so that when the said first non-fluorescent agent and said first fluorescent agent are in close proximity, the emission a signal from said first fluorescent agent is quenched.

In a second aspect, the present invention provides method of preparing an object surface coating according to any of the preceding claims, comprising the steps of
a) providing a peptide comprising the first fluorescent agent, the first non-fluorescent agent, the first cleavage site and a reactive alkyne
b) contacting peptide obtained in step a) with a C5-C25 diacrylate comprising an azide group,
c) crosslinking the peptide-diacrylate conjugate obtained in step b) with one or more polymers.

The inventors have found that incorporating into the coating the first fluorescent agent and first-non-fluorescent agent on a diacrylate modified peptide, the synthesis of the object surface coating is more efficient than in prior art methods.

In the prior art it is known to blend to fluorescently labelled polymers and then cross link the blended polymers. In the method according to the invention, it is not necessary to label the polymer directly. This results in a more atom efficient and time efficient synthesis that those of the prior at.

In a third aspect, there is provided an object comprising a object surface coating according to the invention, said object being selected from the group consisting of medical implants, medical instruments, medical swabs, microwell plates, food preparation surfaces, furniture.

The object surface coating of the present invention is suitable for use on a wide range of substrates. The advantage of the present invention is that is can be used to detect the presence of bacterial infection on medical implant, medical instruments and furniture. Suitable furniture is for example hospital beds, hospitals tables operating tables which surfaces are desirable to remain clean and if a pathogenic bacteria is present be quickly detected.

In an embodiment, the object is selected from the group of needles, catheters, guide wires, screws, implant plates and implant pins.

The object surface coating of the present invention is particularly suited to be used on objects that are to be implanted in the body. By using implants that are coated with the coating of the present invention, a bacterial infection can easily be detected and thus the medical practitioner can easily decide on the next course of treatment.

In a fourth aspect, there is provided a method of coating an object comprising the steps of:
a) providing a object surface coating according to the invention,
b) dip coating the object selected from the group consisting of medical implants and medical instruments to be coated with the surface coating from step a),
c) drying said object obtained in step b).

An object according to the present invention may be coated with said polymer coating using techniques such as dip-coating, spray-coating, spin-coating, or solvent casting. Coating techniques involving the chemical grafting of molecules onto the biomaterial surface are also available. Nano-thin coatings based on self-assembled monolayers (SAMs), surface-tethered polymers (polymer brushes), or multilayer coatings based on layer-by-layer assembly offer precise control on the location and orientation of chemical groups and biomolecules on the surface of the coating are commonly known in the art to apply various coatings to orthopedic components and other medical devices for a variety of reasons, see, Handbook of Materials for Medical Devices, Davis, J. R. (Ed.), Chapter 9, "Coatings" 2003.

In a fifth aspect, there is provided a method of coating an object comprising the steps of:
a) providing a object surface coating according to the invention, and
b) contacting an object selected from the group consisting medical swabs, microwell plates, food preparation surfaces, furniture with the surface coating from step a).

In an particularly preferred embodiment the object surface coating is provided in a solvent, for example an aqueous or organic solvent, which can be applied to a surface, for example medical swabs, microwell plates, food preparation surfaces, furniture. The coating can be applied by, for example painting. Alternatively, the coating can be comprised in an adhesive tape. The advantage of application of the coating by painting or by adhesive tape is that a facile and time efficient means of provided an object with a surface coating for the detection of pathogenic microorganisms is provided.

In a sixth aspect, there is provided a method of preparing an object surface coating according to the invention, comprising the steps of:
a) providing an object surface comprising said one or more polymers, said one or more polymers comprising a reactive group A and
b) contacting the object surface according to step a) with the peptide comprising the first fluorescent agent the first non-fluorescent agent, the first cleavage site and a reactive group B complementary to reactive group A, to prepare said object surface coating.

The inventors have found that surfaces coated with alkynyl groups, for example glass surfaces or microtiter plates coated with alkynyl PEG polymers, can react with peptides, which peptide comprising an azido group, said azido group being complementary to the said alkynl group. Surprisingly, this method enables the facile production of peptide coated surfaces, which surfaces release a fluorescent or non-fluorescent agent in the presence of bacteria.

In an embodiment, said reactive group A being chosen from the group consisting of alcohol (OH), thiol (SH), amine ($NH_2$), acid ($CO_2H$), alkyne, alkene, azide, preferably alkyne or azide, more preferably alkyne.

In an embodiment, said reactive group B being chosen from the group consisting of alcohol (OH), thiol (SH) amine ($NH_2$), acid ($CO_2H$), alkyne, alkene, azide, preferably alkyne or azide, more preferably azide.

In an embodiment, the product of the reaction of reactive group A and reactive group B is a group chosen from the group consisting of an ester, amide, carbamate, thioester, maleimide and Michael addition product linkage.

In an embodiment, the peptide comprising the first cleavage site and first fluorescent agent and first non-fluorescent agent further comprises a reactive group A. Said reactive group A is chosen from the group consisting of alcohol, thiol, amine, carboxylic acid, azide or unsaturated hydrocarbon group, for example alkyne or alkene. Said peptide is brought into contact with an object surface coating comprising reactive group B which is complementary to reactive group A. Reactive group B is chosen from the group of alcohol, thiol, amine, carboxylic acid, azide and or unsaturated hydrocarbon group, for example alkyne or alkene. Preferably, the peptide comprises an azide and the object surface comprises an alkyne. The reactive group B may be covalently bound to one or more polymers of the object surface. In the present invention the polymer may be organic or inorganic. Suitable examples of organic polymers are polyethylene glycol, polyethylene glycol diacrylate, polylactide, polyvinyl alcohol, poly DL-lactide-co-glycolide/polyethylene glycol copolymer and combinations thereof. Suitable examples of inorganic polymers are silica polymers for example siloxanes, for example siloxanes with a (—O—$SiR_2$—O)$_n$ repeating unit where R is a hydrocarbyl chain, preferably C1-C20 hydrocarbyl.

In an embodiment, said object surface undergoes a pre-treatment. Said pre-treatment may be a mechanical or chemical. Said pre-treatment improves the surface morphology such as roughness, texture and porosity of, for example metal or plastic surfaces, to improve the bonding of the polymer coating.

In an embodiment, there is provided a method of sensing photon emission from an object according the invention, comprising the step of radiating the object with photons having a wavelength of 650-900 nm and detecting the emitted photons.

When the object surface coating is illuminated with light having a wavelength of 650-900 nm and a pathogenic microorganism is present, which microorganism releases a compound specific for the cleavage site in the object surface coating, a suitable detector will detect the photons from the coating. Such a method provides a facile means to determine the presence of a pathogenic microorganism. The inventive method is advantageous over the methods of the prior art as a labour intensive, costly and time consuming microbiological culture is not necessary in order to establish the presence of, for example, an infection.

In an embodiment there is provided a method of sensing photon emission from an receptacle coated with a object surface coating according to the invention, comprising the steps of contacting the receptacle with a sample of bodily fluid and detecting the emitted photons.

When the object surface coating is contacted with a bodily fluid, for example saliva or urine or extracellular fluid in general, and subsequently illuminated with light having a wavelength of 650-900 nm, and a pathogenic microorganism is present, which microorganism releases a compound specific for the cleavage site in the object surface coating, a suitable detector will detect the photons from the coating.

Such a method provides a facile means to determine the presence of a pathogenic microorganism in the person from which the bodily sample was taken. The inventive method is advantageous over the methods of the prior art as a labour intensive, costly and time consuming microbiological culture is not necessary in order to establish the presence of, for example, an infection.

In another aspect, the there is provided a use of an object according to the invention for detecting the presence of infectious bacteria.

The inventive method is advantageous over the methods of the prior art as a labour intensive, costly and time consuming microbiological culture is not necessary in order to establish the presence of, for example, an infection.

EXAMPLES

The following non-limiting examples show particular embodiments of the present invention as compared to prior art.

Peptide Synthesis

Peptides 1 and 2 were obtained from Cambridge Research Biochemicals (UK) and used without further purification.

Peptide 1: Ac-X-[K(IRDye800RS)]-GLLEFRIVAK (IRDye800RS)-amide, where X is δ-azido-norvaline (SEQ ID NO: 5).

Peptide 2: Ac-X-GLLEFRIVAC(IRDye800CW)amide, where X is δ-azido-L-norvaline, also named (S)-5-azido-2-(Fmoc-amino) pentanoic acid) (SEQ ID NO: 6).

V8 Protease

Bacterial protease was obtained from Sigma-Aldrich (Endoproteinase Glu-C from *Staphylococcus aureus* V8, P2922 SIGMA), also named 'protease V8' or 'V8' in this document.

GranzymB Protease

Human recombinant protease was obtained from Merck-Millepore (368043 Granzyme B, Human, Recombinant, *E. coli*).

Alkyne-Functionalized Glass Slides

Alkyne-functionalized glass microscope slides (1013-1014 alkyne groups/cm2, 75 mm×25 mm) were obtained from Microsurfaces, Inc. and were cut to size by a diamond glass cutter. The slides were stored in a sealed bag in the dark at −20° C. During the experiments the slides were kept in the dark in a desiccator over $P_2O_5$.

Example 1

Attachment of Peptides to Glass Slides

Peptides 1 and 2 were Attached to Glass Surfaces.

Negative Control Experiment, No CuSO4 (No Covalent Conjugation is Possible)

10 µL of peptide stock solution of peptide 1 (10 mg/mL; in DMSO) was mixed with 26.5 µL of sodium ascorbate solution (1 mg/mL; in DMSO/water 1/1) and 13.5 µL of DMSO was added to increase the solubility of the peptide. The final DMSO/water ratio was 73:27. Final peptide concentration was 0.65 mM, final sodium ascorbate concentration was 2.7 mM.

Peptide 1; Conjugation with CuSO4

10 µL of peptide stock solution of peptide 3 (10 mg/mL; in DMSO) was mixed with 12.5 µL of CuSO4 solution (1 mg/mL; in DMSO/water 1/1) and 14 µL of sodium ascorbate solution (1 mg/mL; in DMSO/water 1/1) and 13.5 µL of DMSO was added to increase the solubility of the peptide. Final DMSO/water ratio was 73:27. Final peptide concentration was 0.65 mM, final CuSO4 concentration was 1 mM, final sodium ascorbate concentration was 1.4 mM.

The resulting solution (50 µL) was pipetted onto the glass slide, and the slide was kept in a humidified environment for 1H. The droplet was washed off by rinsing 3× with 1 mL DMSO:H2O 80/20; thereafter, the slide was placed in a washing solution of DMSO:H2O 80/20 and was gently agitated for 1 minute. The washing solution was rinsed off with water (5×1 mL) and the slide was dried by a flow of nitrogen.

The glass slides were characterized using UV-VIS spectroscopy, where only the slides that had been treated with peptide and with CuSO4 showed a residual absorption maximum of typically 0.01-0.05 in the expected wavelength region 600-800 nm.

Example 2

Monitoring Digestion of Peptide 1 by Luminescence Spectroscopy

The cleavage of peptide 1 in the presence of V8 protease and GranzymB protease was monitored in solution by luminescence spectroscopy. Photo-luminescence spectra were measured on a Perkin-Elmer Luminescence Spectrometer LS50 B. Spectra were recorded from 250 to 900 nm, using an excitation wavelength of 720 nm and applying a slit width of 15 nm.

The digestion in solution was performed in a glass vial. 100 µL of stock solution of peptide 1 (10 mg/mL) was diluted with 625 µL $H_2O$ and 250 µL 100 mM phosphate buffer solution (pH=7.8). A sample of 10 µL was taken at t=0. Then, 50 µL of V8 or Granzyme B protease stock solution (25 units, ±25 µg) was added, the mixture shaken and was kept at room temperature. During the time period of the experiment the incubation solution remained clear (no precipitation of dye peptide). At various time points (30 s, 2, 5, 10, 15, 20, 25, 30, 40, 50, 60, 90, 120, 150 and 180 min., and at 18H) a 10 µL incubate sample was taken and was diluted with 3 mL of water. The prepared diluted samples were measured by luminescence spectroscopy, so as to monitor the digestive cleavage of peptide 1. As blanks, cuvettes with water and the same amount of DMSO as the sample solution were used.

In the absence of V8 protease, a background fluorescence of around 1 AU was observed. After 30 s of adding V8 protease, the fluorescence intensity increases to 4 AU and within 6 minutes the fluorescence intensity is 6 AU. This shows that the peptide according to the invention is capable of detecting bacteria within minutes, which is a considerable improvement over the prior art methods, such as ATP based test for organic material (typically 4-8 hours) or bacterial cultures (24 hours).

In the presence of Granzyme B, Peptide 1 is not cut and the background fluorescence of 1 AU was maintained throughout the experiment. Granzyme B is a serine protease present at a normal concentration of 20-4-pg/ml in the blood plasma. The results show that the peptide is selective for the presence of bacterial proteases and is not cleaved in the presence of proteases released by the human body as part of autoimmune responses.

Example 3

Monitoring Digestion of Surface Bound Peptide 1 by Luminescence Spectroscopy

Li-Cor Odyssey CLX equipment was used on site at Westburg (Leusden, N L; Timo Kreike, Moniek Kors). All Odyssey CLX measurements were taken by exciting at 800 nm.

In the presence of V8 protease, the intensity increased from circa 6000 units to 25000 units, indicating that V8 triggers the release of the quencher group from peptide 1.

In the presence of V8 protease, no change in intensity was observed for peptide 2. The intensity observed remains at 8000 units, indicating that although the fluorescent group may be cleaved, the fluorescent group does not diffuse away from the surface, therefore the no decrease in signal is observed so a false negative result is obtained.

The results show that the coating according to the invention is able to detect the presence of bacteria and is not prone to false negative results.

Example 4

Catheter Coating

The object coatings are composed of a PEG polymer (MeO-PEG-alkyne, IRIS biotech) and a peptide bearing a cleavage site and first fluorescent agent and a first non-fluorescent agent. The comparative example does not contain the first non-fluorescent agent.

Peptides were synthesized by standard solid phase peptide synthesis (SPPS) using standard reagents, coupling and purification techniques.

Coupling of the peptide to the first fluorescent agent and first non-fluorescent agent was conducted post peptide purification and facilitated by maleimide coupling to cysteine or amide coupling to lysine.

Coupling of the peptide bearing a cleavage site and first fluorescent agent and a first non-fluorescent agent was conducted using standard azide alkyne Huisgen cycloaddition reaction conditions.

The catheter used was a 14F silicone Foley Catheter which was provided in 6 mm lengths and having a diameter of 4.2 mm. An aqueous slurry of each polymer coating was prepared and each piece of catheter plunged into the slurry mixture. The coated catheters were stored at 20° C. in the dark for 15 minutes prior to repeating the dipping procedure. The process was repeated four times in total. After the final coating, the coated catheters were stored at 35° C. for 48 hours to facilitate drying of the coating.

Example 5

Each coated catheter and one none coated catheter as control, were incubated in the presence of $2 \times 10^6$ colony-forming units (CFU) $ml^{-1}$ of S. auereus for 4 hours. There after coated catheters were removed from the incubator and exposed to a clinical multispectral fluorescence camera (T3-imaging system, SurgOptix BV, Groningen, The Netherlands) with an IVIS Spectrum (excitation: 710 nm, emission: 800 nm, acquisition time 5 s, binning 4, F-stop 2, FOV 21.2).

The results obtained from the IVIS Spectrum and IVIS Lumina II were analyzed with Living Image 4.2. (Caliper L S, Hopkinton Mass., USA). Optimal detection limits were set to the lowest signal at which positive signal was effortlessly discriminated from negative controls. Signal intensity was determined by drawing regions of interests (ROI's) and measuring average counts in these regions. The signal was corrected for background by subtracting the background signal from the signal of interest, referred to in the text as net counts. A strong near infrared signal was, attributed to the first fluorescent agent.

The results are shown in Table 1.

TABLE 1

| Example | Coating | Object | Coating response to S. aureus challenge |
|---|---|---|---|
| 5.1 | NONE | Foley silicone catheter (14F, 4.6 mm) | ++ (tested by microbial culture - 24 hours) |
| 5.2 | G-(Pol)-X-LLEFRIVAC-IRDye800CW (SEQ ID NO: 7) | | − |
| 5.3 | (IRDye800RS)-KG-(Pol)-X-LLEFRIVAK (IRDye800RS) (SEQ ID NO: 8) | | + |
| 5.4 | Ac-(IRDye800CW)CG-(Pol)-X-LLEFRIVAK (IRDyeQC-1) (SEQ ID NO: 9) | | ++ | where Pol is MeO-PEG-alkyne and X is (S)-5-Azido-2-(Fmoc-amino) pentanoic acid

The results show that the coatings according to the invention comprising a non-fluorescent agent with an absorption spectrum overlapping with the emission spectrum of the first fluorescent agent (Example 5.4) lead to very good detection of the presence of pathogenic microorganisms, for example in this case S. aureus. Quenching by the first non-fluorescent agent is strictly dependent on the distance from the first fluorescent agent thus as soon as the first non-fluorescent agent is cleaved, emitted light is detected.

Example 5.4 also shows that the same level of detection can be obtained using the coatings according to the invention as by conventional microbial culture (example 5.1) but the results are obtained much quicker, within 4 hours rather than 24-36 hours as with microbial cultures.

Example 5.3 shows a first fluorescent agent that also functions as a first non-fluorescent agent also provide suitable means to detect microorganisms. However, due to the limited diffusion of the cleaved first fluorescent agent only a weak signal is detected.

Coatings only comprising a first-fluorescent agent do not provide good detection of microorganisms (comparative example 5.2). This is attributed to the slow rate of diffusion of the first fluorescent agent away from the surface thus only a small change in intensity in emitted light is detected.

The invention claimed is:

1. An object surface coating comprising one or more polymers and a peptide covalently linked to at least one of said one or more polymers, said peptide comprising:
a) a cleavage site comprising a specific amino acid motif selected from the group consisting of EFRIK (SEQ ID NO: 1), DFRIK (SEQ ID NO: 2), GIGEFRIK (SEQ ID NO: 3), and GIGDFRIK (SEQ ID NO: 4), wherein said cleavage site is cleaved by a compound specifically provided by a microbe belonging to a group consisting of a limited number of microbial strains, species or genera, and not cleaved by any compound provided by any microbe not belonging to the group, b) a fluorescent agent having an emission wavelength of 650-900 nm, c) a non-fluorescent agent having an absorption wavelength of 650-900 nm, for quenching said emission of said fluorescent agent, wherein cleavage of said cleavage site results in the release of said non-fluorescent agent from the coating, the release of said non-fluorescent agent being indicative for the presence of a microbe belonging to the group; and wherein the microbe is gram positive bacteria.

2. The object surface coating according to claim 1, wherein said one or more polymers are selected from the group consisting of polyethylene glycol, polyethylene glycol diacrylate, polylactide, polyvinyl alcohol, poly DL-lactide-co-glycolide/polyethylene glycol copolymer and combinations thereof.

3. The object surface coating according to claim 1, wherein said peptide is covalently linked via the N- or C-terminus or a side chain to at least one of said one or more polymers by C4-C30 hydrocarbyl linker, preferably via the C-terminus or a side chain, most preferably via the side chain.

4. The object surface coating according to claim 3, wherein the C4-C30 linker comprises a cyclic hydrocarbyl group or a cyclic heterocyclic group, preferably said heterocyclic group is a triazole group.

5. The object surface coating according to claim 1, wherein the cleavage site is cleaved by a compound specifically provided by a microbe belonging to a group consisting of gram positive bacteria or gram negative bacteria.

6. The object surface coating according to claim 1, wherein the cleavage site is cleaved by a compound, being a protease selected from the group consisting of V8 protease, lgA1 protease, and aureolysin.

7. The object surface coating according to claim 1, wherein said fluorescent agent is a cyanine having an emission wavelength of 650-900 nm.

8. The object surface coating according to claim 1, wherein said non-fluorescent agent is a cyanine dye having an absorption wavelength of 650-900 nm.

9. The object comprising a surface coating according to claim 1, said object being selected from the group consisting of medical implants, medical instruments, medical swabs, microwell plates, food preparation surfaces and furniture.

10. The object comprising a surface coating according to claim 1, said object being selected from the group consisting of needles, catheters, guide wires, screws, implant plates and implant pins.

11. A method of preparing an object surface coating of claim 1 comprising one or more polymers and a peptide covalently linked to at least one of said one or more polymers, said peptide comprising:

a) a cleavage site comprising a specific amino acid motif selected from the group consisting of EFRIK (SEQ ID NO: 1), DFRIK (SEQ IN NO: 2), GIGEFRIK (SEQ ID NO: 3), and GIGDFRIK (SEQ ID NO: 4), wherein said cleavage site is cleaved by a compound specifically provided by a microbe belonging to a group consisting of a limited number of microbial strains, species or genera, and not cleaved by any compound provided by any microbe not belonging to said group, b) a fluorescent agent having an emission wavelength of 650-900 nm, c) a non-fluorescent agent having an absorption wavelength of 650-900 nm, for quenching said emission of said fluorescent agent, wherein cleavage of said cleavage site results in the release of said non-fluorescent agent from the coating, the release of said non-fluorescent agent being indicative for the presence of a microbe belonging to said group, the method comprising the steps of:

a) providing an object surface comprising one or more polymers, said one or more polymers further comprising a reactive group A and b) contacting the object surface according to step a) with the peptide comprising the fluorescent agent, the non-fluorescent agent, the cleavage site and a reactive group B complementary to reactive group A so that reactive group A and reactive group B form a covalent linkage to prepare said object surface coating.

12. The method according to claim 11, said reactive group A being chosen from the group consisting of alcohol (OH), thiol (SH), amine (NH2), acid (CO2H), alkyne, alkene, azide.

13. The method according to claim 11, said reactive group B being chosen from the group consisting of alcohol (OH), thiol (SH), amine (NH2), acid (CO2H), alkyne, alkene, azide.

14. A method of sensing photon emission from an object comprising an object surface coating of claim 1 comprising one or more polymers and a peptide covalently linked to at least one of said one or more polymers, said peptide comprising:

a) a cleavage site comprising a specific amino acid motif selected from the group consisting of EFRIK (SEQ ID NO: 1), DFRIK (SEQ IN NO: 2), GIGEFRIK (SEQ ID NO: 3), and GIGDFRIK (SEQ ID NO: 4), wherein said cleavage site is cleaved by a compound specifically provided by a microbe belonging to a group consisting of a limited number of microbial strains, species or genera, and not cleaved by any compound provided by any microbe not belonging to said group, b) a fluorescent agent having an emission wavelength of 650-900 nm, c) a non-fluorescent agent having an absorption wavelength of 650-900 nm, for quenching said emission of said fluorescent agent, wherein cleavage of said cleavage site results in the release of said non-fluorescent agent from the coating, the release of said non-fluorescent agent being indicative for the presence of a microbe belonging to said group, the object selected from the group consisting of medical implants, medical instruments, medical swabs, microwell plates, food preparation surfaces and furniture or selected from the group of needles, catheters, guide wires, screws, implant plates and implant pins, the method comprising the step of radiating the object with photons having a wavelength of 650-900 nm and detecting the emitted photons.

15. A method comprising:

a) providing an object surface coating of claim 1 comprising one or more polymers and a peptide covalently linked to at least one of said one or more polymers, said peptide comprising: a cleavage site comprising a specific amino acid motif selected from the group consisting of EFRIK (SEQ ID NO: 1), DFRIK (SEQ IN NO: 2), GIGEFRIK (SEQ ID NO: 3), and GIGDFRIK (SEQ ID NO: 4), wherein said cleavage site is cleaved by a compound specifically provided by a microbe belonging to a group consisting of a limited number of microbial strains, species or genera, and not cleaved by any compound provided by any microbe not belonging to said group; a fluorescent agent having an emission wavelength of 650-900 nm; and a non-fluorescent agent having an absorption wavelength of 650-900 nm, for quenching said emission of said fluorescent agent, wherein cleavage of said cleavage site results in the release of said non-fluorescent agent from the coating, the release of said non-fluorescent agent being indicative for the presence of a microbe belonging to said group; and b) either dip coating an object selected from the group consisting of medical implants and medical instruments with the object surface coating from step a) or contacting an object selected from the group consisting of medical swabs, microwell plates, food preparation surfaces and furniture with the surface coating from step a).

* * * * *